(12) United States Patent
Ogilvie

(10) Patent No.: US 7,837,739 B2
(45) Date of Patent: Nov. 23, 2010

(54) INTERPOSITIONAL BIARTICULAR DISK IMPLANT

(75) Inventor: William F. Ogilvie, Austin, TX (US)

(73) Assignee: Ascension Orthopedics, Inc., Austin, TX (US)

( * ) Notice: Subject to any disclaimer, the term of this patent is extended or adjusted under 35 U.S.C. 154(b) by 753 days.

(21) Appl. No.: 10/552,951

(22) PCT Filed: Apr. 16, 2004

(86) PCT No.: PCT/US2004/011995

§ 371 (c)(1),
(2), (4) Date: Jun. 22, 2006

(87) PCT Pub. No.: WO2004/093767

PCT Pub. Date: Nov. 4, 2004

(65) Prior Publication Data

US 2006/0241778 A1    Oct. 26, 2006

Related U.S. Application Data

(60) Provisional application No. 60/463,802, filed on Apr. 18, 2003.

(51) Int. Cl.
*A61F 2/42* (2006.01)
(52) U.S. Cl. ................ 623/21.15; 623/21.11
(58) Field of Classification Search ............. 623/21.19, 623/21.15, 21.11, 14.12
See application file for complete search history.

(56) References Cited

U.S. PATENT DOCUMENTS

| | | | | |
|---|---|---|---|---|
| 4,198,712 A | * | 4/1980 | Swanson | 623/21.14 |
| 5,645,605 A | * | 7/1997 | Klawitter | 623/21.15 |
| 5,782,927 A | | 7/1998 | Klawitter et al. | |
| 5,888,203 A | * | 3/1999 | Goldberg | 623/13.11 |
| 6,159,247 A | * | 12/2000 | Klawitter et al. | 623/21.15 |
| 6,425,920 B1 | | 7/2002 | Hamada | |
| 6,436,146 B1 | | 8/2002 | Hassler et al. | |
| 6,699,292 B2 | | 3/2004 | Ogilvie et al. | |

(Continued)

FOREIGN PATENT DOCUMENTS

EP    0 314 593    10/1988

(Continued)

OTHER PUBLICATIONS

Eaton et al., "Replacement of the Trapezium for Arthritis of the Basal Articulations", *The Journal of Bone and Joint Surgery* (1979), vol. 61-A, No. 1, pp. 76-82.

(Continued)

*Primary Examiner*—David Isabella
*Assistant Examiner*—Joshua Levine
(74) *Attorney, Agent, or Firm*—Fitch, Even, Tabin & Flannery

(57) ABSTRACT

An interpositional biarticular disk implant (11) having a circular peripheral rim, a generally toroidal axial center opening (13) and convex upper and lower surfaces (15, 17) is implanted between resected concave surfaces of the metacarpal base and the trapezium or other carpal bone in a CMC joint replacement. The disk (11) is anchored in operative position through the use of a flexible cord, such as a harvested tendon that passes through the center opening (13) and through osseous passageways created in the two facing bones.

20 Claims, 2 Drawing Sheets

U.S. PATENT DOCUMENTS

| | | | |
|---|---|---|---|
| 7,004,971 B2* | 2/2006 | Serhan et al. | 623/17.16 |
| 2002/0035400 A1* | 3/2002 | Bryan et al. | 623/17.15 |
| 2003/0009224 A1 | 1/2003 | Kuras | |
| 2003/0093152 A1* | 5/2003 | Pedersen et al. | 623/14.12 |
| 2005/0033426 A1 | 2/2005 | Ogilvie et al. | |
| 2005/0119757 A1 | 6/2005 | Hassler et al. | |

FOREIGN PATENT DOCUMENTS

| | | |
|---|---|---|
| EP | 1 112 753 | 1/2001 |
| FR | 2 711 511 | 10/1993 |
| WO | WO 97/42895 | 5/1997 |
| WO | WO 98/56317 | 5/1998 |

OTHER PUBLICATIONS

Trumble et al., "Thumb Trapeziometacarpal Joint Arthritis: Partial Trapeziectomy With Ligament Reconstruction and Interposition Costochondral Allograft", *Journal of Hand Surgery* (2000), vol. 25A, No. 1, pp. 61-76.

European Patent Office, "Supplementary European Search Report", issued in connection with corresponding European Application No. EP04759993, dated August 6, 2010, 2 pages.

* cited by examiner

INTERPOSITIONAL BIARTICULAR DISK IMPLANT

This invention relates generally to a Interpositional Biarticular Disk (IBD) which is intended for implantation as an interpositional joint spacer for the carpometacarpal (CMC) joint of the hand, particularly the thumb, as well as corresponding tarsometataral (TMT) joints of the foot.

BACKGROUND OF THE INVENTION

The scaphoid is a bone of the wrist aligned with the thumb which is located in the proximal carpal row of bones, and the second or distal carpal row of bones contains the trapezium which is attached to the metacarpal bone of the thumb. In a case of fracture or severe arthritic pain at the base of the thumb, there has been some tendency to remove the arthritic articular surfaces of the joint between the trapezium and this metacarpus (which is referred to as the CMC joint) or to remove the entire trapezium; however, when this occurs, stability is lost. Burton and Pellegrini have described a tendon interpositional arthroplasty technique for removing the trapezium and preventing the base of the metacarpus from rubbing on the scaphoid, see Burton et al. "Surgical Management of Basal Joint Arthritis of the Thumb. Part II. Ligament Reconstruction with Tendon Interposition Arthroplasty," *J. Hand Surg* 11A:324-32 (1986), however, the results are felt to be less than satisfactory. U.S. Pat. No. 6,436,146 (Aug. 20, 2002) shows a wide variety of prosthetic implants designed for use in orthopedic joints, particularly joints of the hand, many of which have convex opposite surfaces; these suggested implants have a variety of different configurations in transverse sectional view and may be circular or oval in plan view. In FIG. 18B, there are shown 2 implants for CMC joints, which have the shapes shown in either FIG. 2A or 2C or FIGS. 10A and 10B. However, in the region of the CMC joint, it is felt that the resultant overall stability of such an implant shape is insufficient for patient satisfaction. Better solutions to this problem have thus been sought.

SUMMARY OF THE INVENTION

The invention provides a one component implant having biconvex articular surfaces which respectively bear against appropriately resected facing surfaces of the base of the metacarpus and the carpal bone segment, e.g. the trapezium, or between the articular surfaces which form the corresponding joints of the foot. This biconvex design allows for both flexion-extension joint motion and abduction-adduction joint motion. A hole is provided that extends through the implant at the axis of symmetry and smoothly flairs into each of the convex articular surfaces; it provides a means of stabilizing the implant against potential dislocation by passing a flexible cord or harvested tendon through this central hole in the implant.

In one particular aspect, the invention provides a surgically implantable prosthesis designed to replace a CMC joint, which implant comprises: a disk having a pair of convex surfaces and an axial, flaring hole which extends therethrough from surface to surface to accommodate a flexible cord that is passed through passageways in the metacarpus and the trapezium or other carpal bone, which once surgically implanted allows the metacarpus to flex relative to the trapezium or other carpal bone enough for useful hand function, with each bone sliding on the respective mating convex surface of the disk while the flexible cord conforms to the flaring surface of the axial hole in the plane of flexion.

In another particular aspect, the invention provides a surgically implantable bone prosthesis designed to replace a CMC or TMT joint, which implant comprises: a disk having a pair of convex surfaces and an axial, flaring opening which extends therethrough from convex surface to convex surface to accommodate a flexible cord that is passed through passageways created in the proximal bone of the digitus and in the trapezium or other carpal or tarsal bone, which disk once surgically implanted allows said proximal bone to flex relative to said other bone enough for useful hand or foot function, with each bone sliding on the respective mating convex surface of the disk while the flexible cord conforms to the flaring surface of the axial hole in the plane of flexion.

In a further particular aspect, the invention provides a method for repairing a deteriorated joint of the hand or foot by implanting a biarticular disk of the structure defined above.

DETAILED DESCRIPTION OF THE PREFERRED EMBODIMENTS

Figure 2:
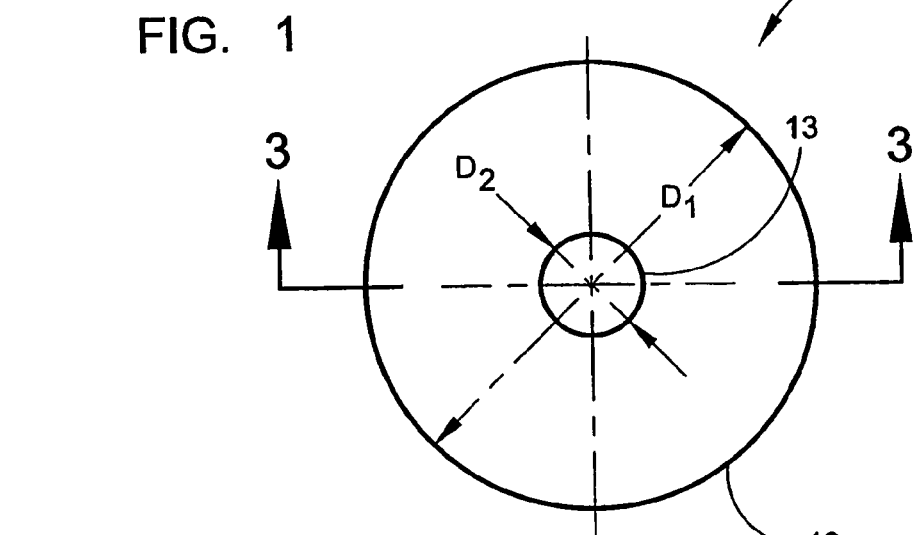
FIG. 2 is a plan view of the implant of FIG. 1.
Figure 3:
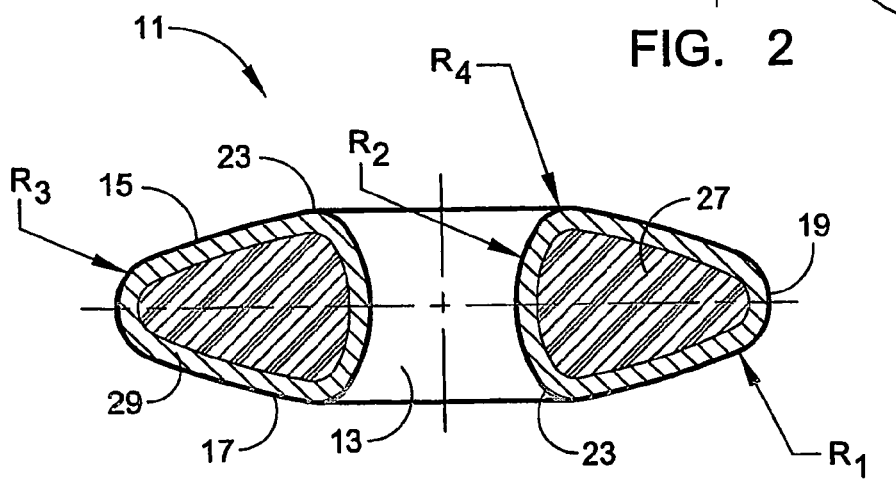
FIG. 3 is a sectional view taken generally along line 3-3 of FIG. 2.

The invention provides an integral disk implant of 11 a biconvex shape that is designed to provide a stable CMC joint between resected surfaces of the base of the metacarpus of the thumb and the trapezium. The implant 11 is also suitable for use to repair the CMC joint of one of the four fingers as well as to repair a corresponding tarsometataral (TMT) joint in the foot. The disk is shown perspectively in FIG. 1, in plan view in FIG. 2 and in a cross sectional view in FIG. 3. It can be seen from the drawings that the implant 11 has the plan shape of a circular disk having a central axial opening 13; upper and lower surfaces 15, 17 of the disk, are both of convex spherical curvature. The peripheral rim 19 of the disk is circular and is curved in 2-dimensions, having a shape that is generally spheroidal while providing a curvature that smoothly joins to the edge regions of the upper and lower convex surfaces to the arcuate rim, as best seen in FIG. 3. The central opening 13 through the disk is a surface which is an internal surface section of a torus in its preferred embodiment, although other equivalent surfaces may be employed; for example, the opening 13 could have a short central circular cylindrical section with toroidal end sections. Short annular transitional surfaces 23 at the upper and lower ends of the axial opening 13 smoothly join the end surfaces of the toroidal opening to the respective convex upper and lower surfaces 15, 17, which are preferably sections of the surface of a sphere.

From a dimensioning standpoint and to accommodate human hands of different sizes, the implants 11 are preferably manufactured in a range of sizes. It is contemplated that a similar size range would be fabricated for foot joint implants. In an implant of this character, it is most desirable that the edge of the implant reasonably close match the edge of the cavity resected in the facing surfaces of the two bones. Too small an implant will not adequately cover the end of the bone and might have a tendency to subside into the bone, whereas too large a diameter implant might have a tendency to limit the range of motion of the joint. Generally, the sizes will range between about 1 cm and about 2 cm in diameter, i.e. diameter $D_1$ in FIG. 2; for example, implants of 14, 16 and 18 mm diameters may be chosen for production. The diameter of the opening 13 is held constant for the different size implants to best accommodate a tendon which might be harvested from the hand of the patient and used to anchor the implant; $D_2$ is this dimension which is interior diameter of the toroidal surface of the axial opening in the preferred configuration, which is about 3±0.5 mm. The convex upper and lower surfaces 15, 17 are preferably sections of the surface of the same sphere so that the radii of curvature ($R_1$) are equal to each other. This allows the implant 11 to be installed in either orientation. As the diameter increases from the smallest size, it can be seen that the radius of curvature $R_1$ would need to be increased for the larger size implants if one desired to maintain the height or the thickness about the same. However, it was instead found that it would be advantageous to manufacture all of implants of a set (e.g. for CMC joints for the thumb) with $R_1$ being held as a constant spherical radius; this arrangement allows the bone preparation of the base of the metacarpus and the distal portion of the trapezium to be done only once while accommodating implants of different diameters of the entire set without further bone preparation, and this allows the implant 11 to be installed in either orientation. Moreover, a tool can be provided to resect the trapezium and the base of the metacarpal simultaneously. It is also found to be desirable to provide some implants in the set of the same diameter, but different thickness, for purposes of tension adjustment. As a result, the surgeon is able to interchange certain of the different size implants of the same diameter to adjust the tension of the soft tissues crossing the joint and obtain the best fit.

As can be seen from FIG. 3, the disk is relatively shallow in curvature. The radius ($R_1$) of spherical convex surfaces 15, 17 should be at least about twice the length of the radius of the circular disk 11 (i.e. one-half of $D_1$). It should likewise be at least about twice the height of the disk 11.

The table which follows sets forth the variable dimensions (in mm) for a preferred set of 5 implants of different sizes which are suitable for a CMC joint replacement of the thumb or a finger of similar size:

TABLE

| Size No. | Diameter $D_1$ | Thickness/Height | Torus Radius - $R_2$ |
|---|---|---|---|
| 14 × 7 | 14 | 7 | 5.26 |
| 16 × 7 | 16 | 7 | 5.26 |
| 18 × 7 | 18 | 7 | 5.26 |
| 16 × 9 | 16 | 9 | 6.30 |
| 18 × 9 | 18 | 9 | 6.30 |

As mentioned above, the interior diameter of the toroidal surface that forms the axial opening 13 is preferably held constant; and it is more preferably between about 3 and about 3.5 mm. The curvature of the toroidal surface, i.e. the radius of the circle that is revolved to create the surface, is chosen as a function of the thickness of this implant, and the radius of this circle is preferably about 15% to about 30% less than the thickness of the implant and more preferably about 20 to about 25% less. This dimension is indicated as the radius $R_2$ in FIG. 3, which most preferably is about 5.25 mm and about 6.3 mm for implants of 7 mm and 9 mm thickness, respectively. The peripheral rim edge may have a curvature in the vertical plane, i.e. the plane which includes the axial centerline of the disk, about the same as the radius of the disk itself as seen in plan view in FIG. 2; this is represented as radius $R_3$. Thus, the rim edge section may preferably be a short segment of a spherical or spheroidal surface.

There should also be a smooth transition between the upper and lower convex surfaces 15, 17 and (a) the surface that defines the axial opening 13 and (b) that defining the peripheral rim 19. The convex arcuate surfaces joining the main upper and lower surfaces 15, 17 and the axial opening 13 are considered to be the more important of these transition surfaces, and in order to ensure integrity and longevity of operation of the implant, this transition should blend very smoothly with the edge of the torus. Preferably, the radius of curvature $R_4$ of this arcuate surface will vary between about 0.7 and about 3 millimeters to achieve the smooth transition. This combination of the biconvex disk face surfaces and the toroidal flaring axial hole allows the metacarpus to easily flex, moving relative to the trapezium sufficiently to effect useful hand function, with each bone sliding on its respective, mating convex surface of the disk, while a flexible cord passing through the axial opening 13 follows and conforms to the portion of the toroidal surface of the axial opening in the plane of flexion. This design, which facilitates such relative motion between implant and bone surfaces, maximizes the range of joint flexion while minimizing the amount of stretching force that is being applied to the flexible cord passing through the implant because the effective center of bending will no longer be at the edge of the rim of the implant as a result of such relative shifting of the implant. Moreover, the toroidal shape of the flaring opening against which the flexible cord, preferably a harvested tendon, bears significantly minimizes undesired stretching at this location. The other two transition surfaces flanking the rim 19 will generally also be in this range.

For constructing the implant, although a variety of materials may be used, it has been found that a machined graphite substrate 27 which is coated overall with a completely encasing pyrocarbon layer 29 provides the preferred solution to meet the demands to which such an implant 11 will be subjected. The pyrocarbon layer 29 encases the graphite substrate 27 and thus provides an external implant surface which interfaces excellently with bone and soft tissues. Pyrocarbon exhibits a number of attributes that are deemed very desirable for an orthopedic prosthesis. These characteristics include: (1) high strength, (2) high wear resistance, (3) resistance to cyclic fatigue, (4) biocompatibility (with both blood and bone), (5) a modulus of elasticity similar to cortical bone, (6) an ability to support direct bone apposition, and (7) low friction on polished surfaces (e.g. coefficient of friction about 0.15). Although various medically approved dense pyrocarbons may be used, such as that sold under the trademark Pyrolite, pyrocarbon made in accordance with the teachings of U.S. Pat. No. 5,677,061 is particularly preferred; it is commercially available as On-X™ pyrocarbon. Alternatively, but less desirably, the implant could also be constructed of CoCr alloys, titanium, ceramics such as alumina, or even a suitable polymeric material.

The pyrocarbon layer 27, which completely encapsulates the graphite substrate 29, differs from the substrate in mechanical properties; pyrocarbon is both stiffer and more fracture-resistant than graphite. As a result, the exterior pyrocarbon layer 27 dominates the mechanical and biocompatibility characteristics of the component and provides the desired strength, durability, extreme resistance to wear, and both biological and biomechanical compatibility. Because pyrocarbon is not easily visible on a radiograph, the graphite substrate 29 is preferably machined from a material that is impregnated with a small amount of tungsten (e.g. 10 weight percent, approximately 1 atom percent); this renders the graphite substrate radiopaque and thus clearly visible on a radiograph.

Figure 5:
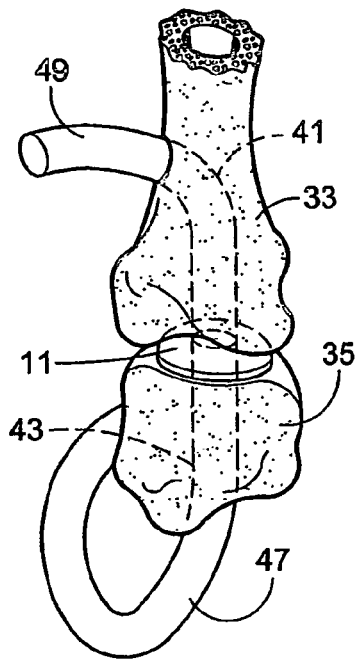
FIG. 5 is a perspective sketch showing implant of FIG. 1 installed at the CMC joint.
Figure 4:
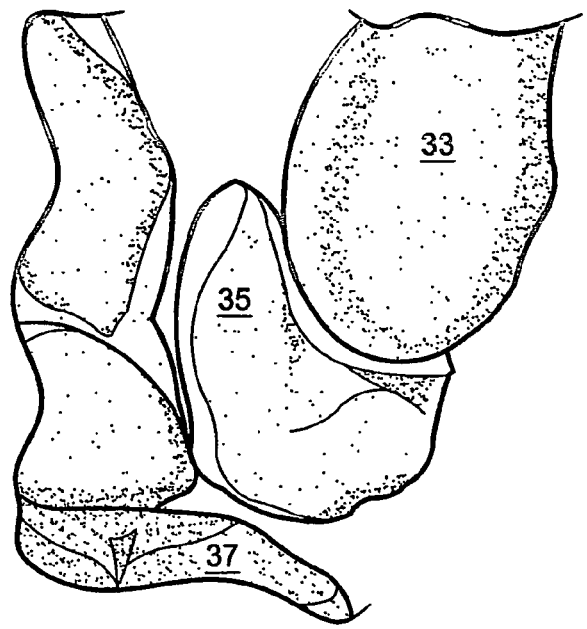
FIG. 4 is a diagrammatic perspective view of a portion of the bone structure of a human right hand, shown from a volar perspective.
Figure 6:
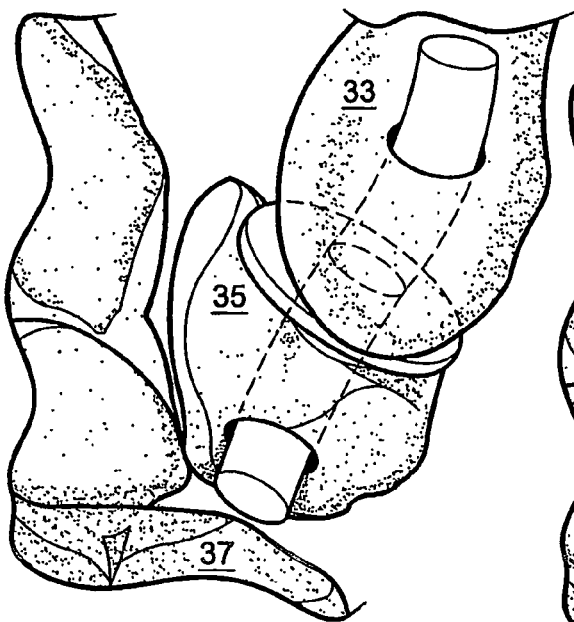
FIG. 6 is a perspective view similar to FIG. 4 showing one manner of installing the implant of FIG. 1.
Figure 7:
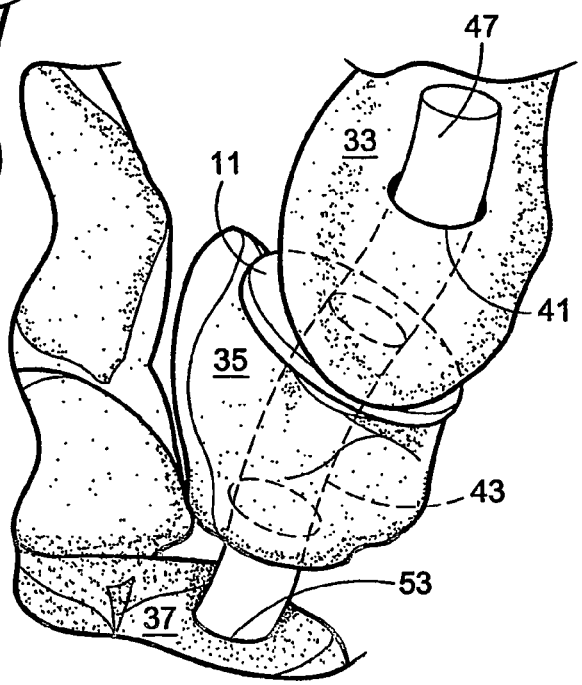
FIG. 7 is a perspective view similar to FIG. 6 showing an alternative method for installing the implant of FIG. 1.

Shown in FIG. 4 is a partial view of the bones of a human hand, i.e. a right hand shown from the palmar aspect. It can be seen that the base of the metacarpus 33 of the thumb articulates against the distal surface of the trapezium 35, the opposite surface of which engages the scaphoid 37. In reconstructing a CMC joint utilizing the implant 11, the base of the metacarpus 33 is resected to provide a concave surface having a curvature of substantially the same radius as the radius of curvature $R_1$ of the particular size implant the surgeon chooses to use; however, by employing a standard radius of curvature for all implants in one set for the convex surfaces 15, 17, e.g. 19 mm, the need to repeat the resection to change the size of the implant is avoided. The distal surface of the trapezium 35 is similarly resected to have a concave surface of the same radius of curvature. A transosseous passageway or tunnel 41 is then created in the metacarpus, and another tunnel 43 is created in the trapezium. One end of each passageway emerges centrally of each of such resected concave surfaces, whereas the opposite end may emerge generally laterally on the respective bone, as seen in FIGS. 5 and 6. As also depicted in FIGS. 5 and 6, a harvested tendon 47 is passed through the transosseous passageway in one of the bones, through the central opening 13 in the implant 11 and then through the passageway in the other bone to anchor the implant in the void created by the bone removal during resection. The convex upper and lower surfaces 15, 17 of the implant articulate smoothly against the resected concave surfaces of the facing bones at the CMC joint. The tendon 47 can either be sutured to itself, or if it is harvested from the vicinity of the CMC joint so that the end of the still attached tendon is used and its free end is passed through the two bones and the implant (in either direction), the free end 49 can then be tied off or knotted as depicted schematically in FIG. 5. In an alternative version of this procedure, which is depicted in FIG. 7, the tunnel in the trapezium is directed generally straight through the trapezium rather than out one side as in FIG. 6, and another transosseous tunnel or passageway 53 is created in the scaphoid 37 in alignment with that in the trapezium 43. The harvested tendon 47 or other cord is then routed through both the scaphoid 37 and the trapezium 35 on one side of the implant 11.

As earlier indicated, the removal of arthritic articular surfaces of a CMC joint and their replacement by an appropriately anchored implant 11 of the design disclosed herein is effective to relieve pain during the patient's subsequent motion of the joint. This implant 11 serves as a functional, robust and durable prosthesis that addresses complex and multifaceted problems involving anatomical, biocompatible, biomechanical and surgical considerations. From a functional perspective, the mechanical design considerations address joint range of motion, center of rotation, force transmission capabilities, and wear resistance of the implant. Anatomical issues involve the articulating surfaces and the need for a range of sizes to accommodate anthropomorphic variations. Surgical concerns take into account the need for minimal bone removal and the preservation of the surrounding soft tissues.

The design objective for the implant is of course to relieve pain, allow a useful range of motion, and restore to the patient a high degree of hand functionality. The implant procedure is also able to reestablish the length of the thumb after diseased and damaged trapezial and metacarpal articular surfaces have eroded. The size and geometric features of the component, and the strength and wear resistance of the materials were evaluated under test conditions deemed representative of rigorous and demanding anatomically relevant constraint and loading situations and found to be adequate.

The implant surface is finished to an average surface roughness $R_A=5.7\pm2.3$ microinch (145±59 nm). In the presence of a lubricating medium, i.e. synovial fluid, such a finish results in very low friction during articulation.

Figure 1:
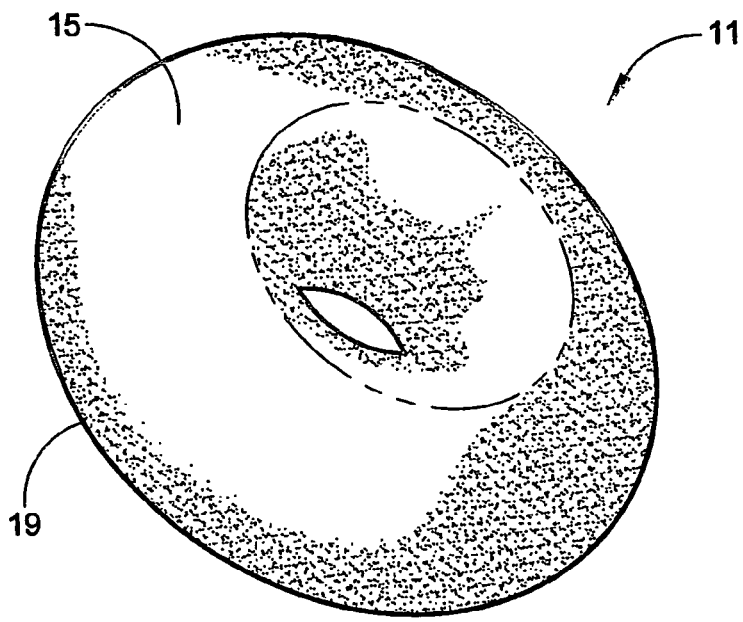
FIG. 1 is a perspective view of an implant embodying various features of the invention.

In summary, the implant's two convex articular surfaces 15, 17 terminate in a peripheral rim 19 and central opening or lumen 13, as shown in FIG. 1. These spherical articular surfaces contact the resected surfaces of the metacarpus and the trapezium or other respective bone in the hand, thus providing a robust load transmission path. The design helps preserve the ligaments and the tendon attachments on the base of the metacarpus and distal surface of the trapezium or other carpal bone, while replacing the resected bone volume to preserve the length of the thumb or digitus, as would also be the case for repair of a TMT joint.

The functional center of rotation of the joint of this design is established so as to recreate the two anatomic centers of rotation, one for flexion-extension and one for adduction-abduction. This is accomplished through the selection of the curvature of the biconvex articular surfaces 15, 17 which facilitates the relative movement against the resected ends of the bones. Such desired centers of rotation have been found to result from the use of implants wherein the radius of curvature $R_1$ of these sections of convex spherical surface is between about 13 and about 23 mm, preferably between about 15 mm and 22 mm and more preferably about 19 mm±0.5 mm, in combination with complementary toroidal surfaces at the axial opening that minimize constraint that might be otherwise exerted by the tendon.

When accurately placed and securely anchored, this interpositional joint implant has been found to excellently reestablish functional joint mechanics. The implant can be so installed so as to preserve the insertion sites for the ligaments and the APL tendon on the base of the metacarpus, and preservation of these soft tissues contributes significantly to joint stability and function. A rehabilitated CMC joint using the implant 11 accommodates an anatomic range of active motion for a CMC joint of 53° flexion-extension, 42° of abduction-adduction, and 17° of rotation.

To ensure proper and accurate implantation of the implant 11, ancillary supplies and instrumentation are provided to assist the surgeon. Transparent radiographic overlays are preferably made available to assist the surgeon in determining, pre-operatively, the appropriate implant size required. In addition, an instrument package should be provided which includes an awl, an articular surface forming broach, and sizing trials. During the surgical procedure, the resected surfaces of the metacarpus and trapezium are shaped with the broach so that the implant will mate accurately with the cut surface of the bones.

For a CMC joint replacement, the implant 11 is designed to articulate against the resected surfaces of the metacarpus and of the trapezium or other carpal bone; thus, it will bear against cortical bone. Wear tests demonstrate that the wear performance of On-X pyrocarbon, when bearing on cortical bone, is excellent. Strength tests conducted on the implant in the form of strength and fatigue endurance tests show the implant 11 is robust, durable and capable of supporting the biomechanically demanding loads experienced in a CMC joint.

Although the invention has been described with respect to certain preferred embodiments, various changes and modifications as would be obvious to one having the ordinary skill in the art may be made without departing from the scope of the invention which is defined solely by the appended claims. For example, although the joint has been described with respect to the replacement of the CMC joint, it should be understood that by changing the relative sizes of the sets of implants, they may also be readily adapted for use in a TMT joint replacement: The disclosures of all U.S. Patents mentioned in this application are incorporated herein by reference.

The invention claimed is:

1. A surgically implantable biarticular disk designed to replace a CMC joint, which implant comprises:
an integral disk which is circular in plan view and has a pair of convex spherical articular surfaces, each of which is a section of a sphere, and an axial, flaring hole which extends therethrough from articular surface to articular surface to accommodate a flexible cord that is passed through passageways in the metacarpus and the trapezium or other carpal bone, said convex spherical articular surfaces being interconnected at their peripheries by a curved rim surface which is a segment of a spheroid, which disk is a graphite core coated with wear-resistant pyrocarbon on its articular surfaces and, once surgically implanted in space created by resecting the base of the metacarpus and the distal surface of the trapezium to provide two concave spherical surfaces, allows the metacarpus to flex relative to the trapezium or other carpal bone enough for useful hand function, with each bone sliding on the respective mating convex articular surface of the disk while the flexible cord conforms to the flaring surface of the axial hole in the plane of flexion.

2. The implant of claim 1 wherein said axial flaring opening is a section of a torus.

3. The implant of claim 2 wherein said torus has a radius of curvature which is about 15% to about 30% less than the height of said disk.

4. The implant of claim 2 wherein the radius of curvature of transition surfaces between said toroidal surface and said convex spherical surfaces is between about 0.7 and about 3 mm.

5. The implant of claim 1 wherein the radii of curvature of said pair of convex spherical surfaces are the same.

6. The implant of claim 5 wherein said radius of curvature of each said convex spherical surface is at least about twice the radius of said circular disk and wherein said peripheral rim surface is a segment of a sphere.

7. A method of repairing a deteriorated CMC joint of the thumb, which method comprises:
resecting the base of the metacarpus and the distal surface of the trapezium to provide concave articular surfaces which match the convex articular surfaces of the disk of claim 1, creating passageways in the metacarpus and the trapezium opening into said resected concave articular surfaces, and surgically implanting the implant of claim 1.

8. The method of claim 7 which includes the step of selecting said implant to be implanted from a set of said implants of different sizes but all having substantially the same radius of curvature of said convex surfaces.

9. A surgically implantable biarticular disk designed to replace a CMC or TMT joint, which implant comprises:
an integral circular disk having a pair of convex spherical articular surfaces, each of which is a section of a sphere, and an axial, flaring opening which extends therethrough from convex articular surface to convex articular surface to accommodate a flexible cord that is passed through passageways created in the proximal bone of the digitus and in the trapezium or other carpal or tarsal bone, said convex spherical articular surfaces being interconnected at their peripheries by a curved rim surface which is a segment of a spheroid, which disk is a graphite core coated with wear resistant pyrocarbon on its articular surfaces and, which disk has a modulus of elasticity similar to cortical bone and, once surgically implanted in space created between two resected articular bone surfaces, allows said proximal bone to flex relative to said other bone enough for useful hand or foot function, with each bone sliding on the respective mating convex articular surface of the disk while the flexible cord conforms to the flaring surface of the axial hole in the plane of flexion.

10. The implant of claim 9 wherein said axial flaring opening is a section of a torus.

11. The implant of claim 10 wherein said torus has a radius of curvature which is about 15% to about 30% less than the height of said disk.

12. The implant of claim 10 wherein transition surfaces between surfaces of said torus and said convex spherical surfaces have a radius of curvature between about 0.7 and about 3 mm.

13. The implant of claim 9 wherein the radii of curvature of said pair of convex spherical surfaces are the same and wherein said peripheral rim surface is a segment of a sphere.

14. The implant of claim 13 wherein said radius of curvature of each said convex spherical surface is at least about twice the radius of said circular disk.

15. A method of repairing a deteriorated CMC or TMT joint which method comprises: resecting the base of the proximal bone of the digitus and the distal surface of the carpal or tarsal bone to provide concave articular surfaces which match the convex articular surfaces of the disk of claim 9, creating passageways respectively in said bones which open into said resected concave articular surfaces, and surgically implanting the biarticular disk of claim 9.

16. A method of repairing a deteriorated CMC joint of the thumb, which method comprises:
resecting the base of the metacarpus and the distal surface of the trapezium to provide concave articular surfaces of similar spherical curvature, and creating passageways in the metacarpus and the trapezium which will open into said resected concave surfaces,
providing a circular disk of having a pair of convex spherical articular surfaces of the same spherical curvature as said resected articular surfaces and an axial, flaring hole which extends therethrough from surface to surface to accommodate a flexible cord, said convex spherical articular surfaces being interconnected at their peripheries by a curved rim surface which is a segment of a spheroid, which disk is a graphite core coated with wear resistant pyrocarbon on its articular surfaces and, and
surgically implanting said disk, which disk once surgically implanted allows the metacarpus to flex relative to the trapezium, as each resected concave articular surface slides on the respective convex articular surface of said disk, enough for useful hand function.

17. The method of claim 16 which includes the step of selecting said disk to be implanted from a set of disks of different sizes but all having substantially the same radius of curvature of said convex surfaces.

18. The method of claim 16, which includes the step of passing a flexible cord through the passageway created in the metacarpus, the flaring axial opening and the passageway created in the trapezium so that the flexible cord conforms to the flaring surface of the axial hole in the plane of flexion when each bone slides on the respective mating convex surface of the disk.

19. The method of claim 18 wherein said flexible chord is a harvested tendon.

20. The method of claim 19 wherein said tendon is harvested from the vicinity of the CMC joint where it remains attached and the free end is passed through said passageways and tied off or knotted.

* * * * *